(12) United States Patent
Ouchi

(10) Patent No.: US 8,927,382 B2
(45) Date of Patent: Jan. 6, 2015

(54) PHOTO-SEMICONDUCTOR DEVICE AND METHOD OF MANUFACTURING THE SAME

(75) Inventor: Toshihiko Ouchi, Sagamihara (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/342,304

(22) Filed: Jan. 3, 2012

(65) Prior Publication Data

US 2012/0108004 A1    May 3, 2012

Related U.S. Application Data

(62) Division of application No. 12/567,940, filed on Sep. 28, 2009, now Pat. No. 8,101,954, which is a division of application No. 11/087,747, filed on Mar. 24, 2005, now Pat. No. 7,615,787.

(30) Foreign Application Priority Data

Mar. 26, 2004 (JP) ................................. 2004-092403

(51) Int. Cl.
*H01L 21/331* (2006.01)
*H01L 21/8222* (2006.01)
*H01L 31/101* (2006.01)
*G01J 3/02* (2006.01)
*G01J 3/42* (2006.01)
*G01N 21/35* (2014.01)
*H01L 31/0224* (2006.01)
*H01L 31/0232* (2014.01)

(52) U.S. Cl.
CPC ............. *H01L 31/101* (2013.01); *G01J 3/0256* (2013.01); *G01J 3/42* (2013.01); *G01N 21/3581* (2013.01); *H01L 31/022408* (2013.01); *H01L 31/0232* (2013.01)
USPC ............. 438/317; 438/604; 438/606; 257/76; 372/4

(58) Field of Classification Search
CPC ... H01L 21/331; H01L 21/8222; H01L 21/28; H01L 21/3205
USPC .......... 438/317, 604, 606, FOR. 134; 257/76; 372/4
See application file for complete search history.

(56) References Cited

U.S. PATENT DOCUMENTS

| 5,416,327 A | 5/1995 | Weiss et al. ................... 850/307 |
| 5,701,325 A | 12/1997 | Ouchi et al. .................... 372/96 |

(Continued)

FOREIGN PATENT DOCUMENTS

| JP | 10-104171 | * | 4/1998 |
| JP | 2002-098634 | | 4/2002 |
| JP | 2002-223017 | | 8/2002 |

OTHER PUBLICATIONS

S. Matsuura et al., "Generation of Coherent Terahertz Radiation by Photomixing in Dipole Photoconductive Antennas", *Appl. Phys. Lett.*, vol. 70, No. 5, pp. 559-561, Feb. 3, 1997.

*Primary Examiner* — Mamadou Diallo
*Assistant Examiner* — Joannie A Garcia
(74) *Attorney, Agent, or Firm* — Fitzpatrick, Cella, Harper & Scinto

(57) ABSTRACT

A method of manufacturing a photo-semiconductor device that has a photoconductive semiconductor film provided with electrodes and formed on a second substrate, the semiconductor film being formed by epitaxial growth on a first semiconductor substrate different from the second substrate, the second substrate being also provided with electrodes, and the electrodes of the second substrate and the electrodes of the photoconductive semiconductor film being held in contact with each other.

5 Claims, 9 Drawing Sheets

(56) References Cited

U.S. PATENT DOCUMENTS

| | | | |
|---|---|---|---|
| 5,789,750 A * | 8/1998 | Nuss | 250/338.1 |
| 5,850,408 A | 12/1998 | Ouchi et al. | 372/27 |
| 6,046,096 A | 4/2000 | Ouchi | 438/510 |
| 6,055,251 A | 4/2000 | Ouchi et al. | 372/28 |
| 6,089,442 A | 7/2000 | Ouchi et al. | 228/180.1 |
| 6,222,868 B1 | 4/2001 | Ouchi et al. | 372/50 |
| 6,320,691 B1 | 11/2001 | Ouchi et al. | 359/237 |
| 6,477,286 B1 | 11/2002 | Ouchi | 385/14 |
| 6,507,594 B1 | 1/2003 | Furukawa et al. | 372/36 |
| 6,573,737 B1 | 6/2003 | Lyon et al. | 324/753 |
| 6,771,677 B2 | 8/2004 | Furukawa et al. | 372/36 |
| 6,836,579 B2 * | 12/2004 | Ouchi | 385/14 |
| 6,873,165 B2 | 3/2005 | Lee et al. | 324/750 |
| 6,970,612 B2 | 11/2005 | Ouchi | 385/14 |
| 7,446,861 B2 | 11/2008 | Ouchi | 356/5.01 |
| 2004/0184495 A1 * | 9/2004 | Kondo | 372/36 |
| 2005/0058166 A1 | 3/2005 | Hu et al. | 372/43 |
| 2005/0233490 A1 | 10/2005 | Kasai et al. | 438/46 |
| 2006/0056757 A1 * | 3/2006 | Ouchi | 385/14 |

* cited by examiner

LIGHT PULSE

THz PULSE

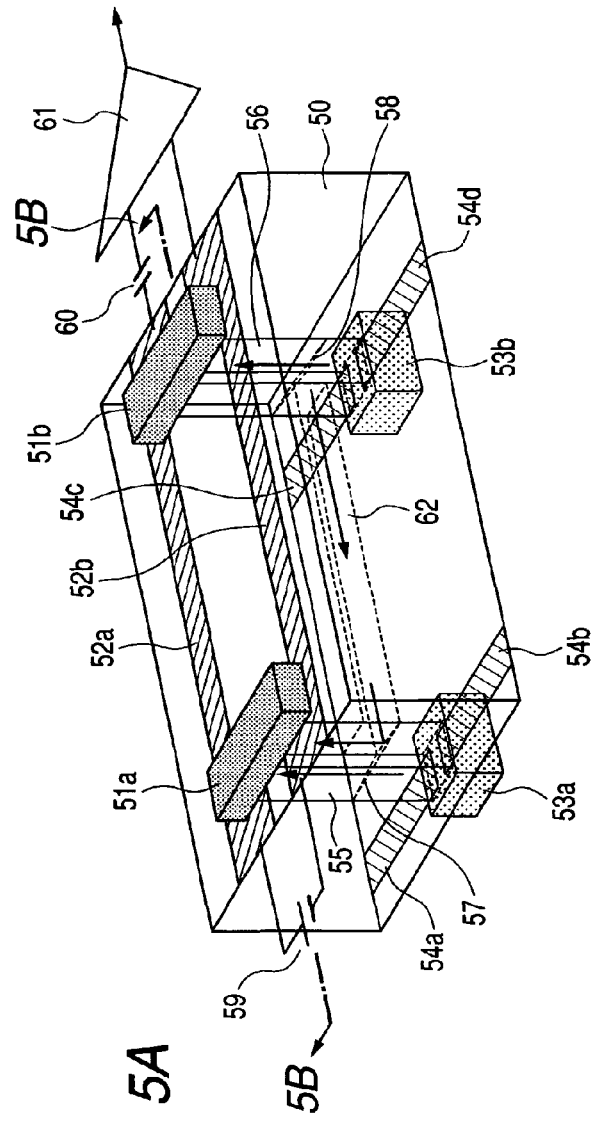
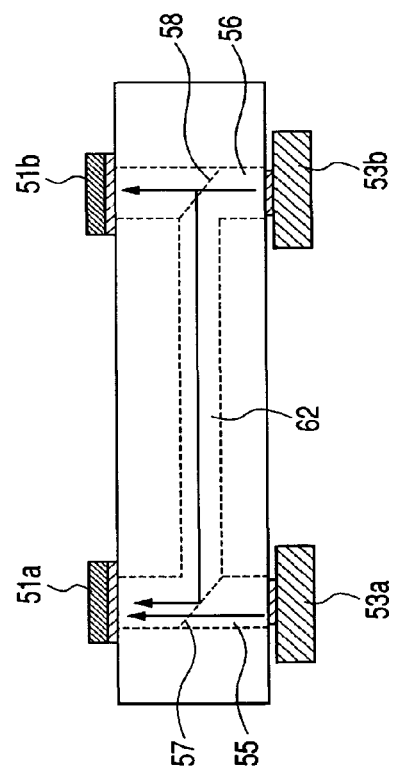
FIG. 5A
FIG. 5B

PHOTO-SEMICONDUCTOR DEVICE AND METHOD OF MANUFACTURING THE SAME

RELATED APPLICATIONS

This application is a divisional of application Ser. No. 12/567,940, filed Sep. 28, 2009, which is a divisional of 11/087,747, filed Mar. 24, 2005 (now U.S. Pat. No. 7,615, 787, issued Nov. 10, 2009), claims benefit of both of those applications under 35 U.S.C. §120, and claims priority benefit under 35 U.S.C. §119 of Japanese Application No. 2004-092403, filed Mar. 26, 2004. The entire contents of each of the above-mentioned applications are incorporated herein by reference.

BACKGROUND OF THE INVENTION

1. Field of the Invention

This invention relates to a photo-semiconductor device having a function of transmitting/receiving a high frequency electric signal mainly in a frequency range between milli-meter and tera-hertz waves and a method of manufacturing the same.

2. Related Background Art

So-called non-destructive sensing technologies using electromagnetic waves of a frequency range between milli-meter and tera-hertz waves (30 GHz to 30 THz) have been developed in recent years. Technologies using electromagnetic waves of such a frequency range include those for imaging, using fluoroscopic inspection apparatus that are safe and can replace X-ray apparatus, those for examining the internally bonded states of substances by determining absorption spectra and complex dielectric constants, those for analyzing biomolecules and those for evaluating carrier densities and carrier mobilities. Position sensing technologies have also been developed for anti-collision radars using 70 GHz band waves, or milli-meter waves.

For example, Japanese Patent Application Laid-Open No. 2002-98634 discloses a two-dimensional imaging apparatus designed to spatially expand a pulsed beam of light in a tera-hertz frequency range, irradiating it onto a specimen and observing a two-dimensional fluoroscopic image in a time domain. FIG. 9 of the accompanying drawings is a diagram schematically illustrating the disclosed apparatus. The pulsed visible beam of light emitted from a light source 121 is branched by a half mirror 128, and one of the branched light beams, or light beam 121b, is irradiated onto a tera-hertz light source 122, which is referred to as a photoconductive switch and is adapted to convert a light pulse into an electromagnetic pulse that corresponds to the envelop of the light pulse. The generated tera-hertz beam of light is transmitted through a specimen 125 by means of an optical system 123 and converged to a tera-hertz beam detector 126. On the other hand, the other output 121a is delayed by a movable mirror 124 and irradiated onto the tera-hertz beam detector 126. The time domain gauging can be performed by gating control that allows the reception signal of the tera-hertz beam to be taken out only at the timing of irradiation of the light pulse. A photoconductive switch having the structure same as that of the tera-hertz beam generator 122 is used as the tera-hertz beam detector 126.

A photoconductive switch element disclosed in Japanese Patent Application Laid-Open No. 10-104171 and realized by arranging an antenna, which operates also as an electrode, on a photoconductive film that is formed on a substrate can suitably be used to generate and detect a tera-hertz beam of light. FIG. 10 of the accompanying drawings schematically illustrates such a photoconductive switch element. As shown in FIG. 10, the substrate 130 of the photoconductive switch element is a silicon-on-sapphire structure that is radiation-treated. In other words, a silicon film that is a photoconductive material is formed on a sapphire substrate. LT-GaAs grown on a GaAs substrate at low temperature is often used as photoconductive film in place of the silicon-on-sapphire structure. The dipole antenna 138 formed on the surface comprises a pair of dipole feeder lines 138a and 138b and a pair of dipole arm sections 139a and 139b. A tera-hertz (THz) pulse is generated when the light pulse is converged to the gap 133 and a voltage is applied to the gap 133 so that it is possible to detect the THz pulse by detecting a photocurrent by means of current amplifier 134 without applying a voltage. Substrate lens 136 takes a role of coupling an electromagnetic wave from a slab mode (substrate mode) of being confined to substrate 130 to a radiation mode of being radiated to free space and also a role of controlling the radiation angle of electromagnetic propagation mode in space.

On the other hand, a wavelength-variable tera-hertz beam of light showing a high degree of spectrum purity is required for producing a spectral effect in a wavelength domain instead of gauging in a time domain. Applied Physics Letters 70(5), pp. 559-567 (1997) describes an arrangement for generating a wavelength-variable tera-hertz beam of CW light by generating the difference frequency of two laser beams by mixing that can be used for such an application. An element similar to the one illustrated in FIG. 10, or an arrangement for generating a tera-hertz beam of light by means of a photoconductive switch by applying a voltage between two electric conductors formed on the surface of a compound semiconductor and irradiating a mixing beam of light to the gap between the electric conductors, is used as means for converting a mixing beam of light into a tera-hertz beam of light.

When realizing a photoconductive switch as described above, it has not been possible to select a material and a profile for the substrate freely, because it has been required to form a photoconductive film that is a semiconductor layer on a given substrate in order to produce desired characteristics.

For example, when adding a lens in order to reduce the electromagnetic wave components that do not radiate into free space in a substrate mode, it is desirable to form a substrate and a lens so as to make them show a substantially same dielectric constant from the viewpoint of the efficiency of taking out an electromagnetic wave. In other words, it is ideally desirable to form a substrate and a lens by means of a same material. Normally, electrically highly resistant Si that shows little wavelength dispersion and little absorption loss in the tera-hertz region works as an excellent lens material. However, it has not been possible to use such an ideal structure because it is not possible to form a photoconductive film that operates satisfactorily on an Si substrate. In other words, reflection of light occurs at the interface of the substrate lens and the substrate of the photoconductive element due to the difference of dielectric constant between them because two different materials have to be used for them.

While the reflectivity of the thin film at the interface of the photoconductive element and free space can be reduced by using a material that shows a low dielectric constant in order to reduce the substrate mode. However, a photoconductive film cannot be formed by using a glass substrate or a plastic substrate showing a low dielectric constant.

A laser beam emitted from a laser has to be converged to a very small spot when it is irradiated onto a photoconductive element. A high output power THz generator can be realized by raising the output power of the laser if the substrate shows a high thermal conductivity. Materials that can be used for a substrate showing such a high thermal conductivity include Si, AlN and SiC because they show a thermal conductivity more than three times of the thermal conductivity of GaAs and sapphire. However, it is not possible to directly form a photoconductive film on any of them.

On the other hand, Si substrates, glass substrates and plastic substrates are excellent substrates in terms of cost and safety for forming hybrid modules by integrally combining photoconductive elements, THz waveform transmission paths and antennas.

SUMMARY OF THE INVENTION

In view of the above identified circumstances, it is therefore the object of the present invention to make it possible to form a photoconductive element on a substrate of any profile, the material of which can be selected from a wide range of materials including Si, glass and plastic, so as to make it operate with an improved efficiency for generation and detection of THz pulses at low cost.

According to the present invention, the above object is achieved by providing a method of manufacturing a photo-semiconductor device comprising preparing an electrode or an antenna operating as an electrode on a photoconductive film formed on a first substrate and subsequently preparing a photoconductive element on a second substrate by bonding the electrode or antenna to the second substrate and removing the first substrate except the photoconductive film.

More specifically, firstly, an electrode formed on a second substrate in advance is bonded to an electrode prepared on a first electrode and subsequently the first substrate is removed by chemical etching. An Si substrate, a glass substrate, a plastic substrate or some other appropriate substrate may be used as the second substrate. The second substrate may show a plate-like profile or a profile similar to that of a semispherical lens. The first substrate is typically prepared by forming an etching-stop layer of AlAs on a substrate of a III-V group compound semiconductor such as GaAs and growing non-doped GaAs that is apt to grow at low temperature as photoconductive film on the etching-stop layer typically by means of molecular beam epitaxy (MBE) process.

Alternatively, a method of manufacturing a photo-semiconductor device may comprise preparing an electrode on a photoconductive film that is formed on a first substrate, bonding the electrode on a third substrate, subsequently removing the first substrate except the photoconductive film, then bonding the photoconductive film to a second substrate and taking out the third substrate for the purpose of integrally forming a photoconductive element on the second substrate.

With either of the above-described two methods, it is possible to integrally form a photoconductive element on an Si semispherical lens as thin film in order to suppress the substrate mode and improve the THz radiation efficiency. Additionally, the thermal characteristics of the element are improved when it is integrally formed on a highly thermally conductive substrate made of AlN or SiC. When film type photoconductive elements according to the invention are integrally formed on a substrate on which high frequency transmission lines such as microstrip lines are arranged, it is possible to provide a compact sensing module at low cost. Additionally, when film type photoconductive elements according to the invention are integrally formed on Si-IC gates that require a high speed switching feature, it is possible to provide an optically addressable high speed IC chip that can be used for optical interconnections.

As described above, according to the invention, it is possible to form a photoconductive element on an appropriate substrate of a material that can be selected from a variety of materials including Si, glass and plastic and whose profile can be defined practically without limitations for the purpose of providing a photo-semiconductor device. Therefore, it is possible to improve the efficiency of generating/detecting terahertz electromagnetic waves at low cost. It is also possible to provide a compact sensing module that is integral with terahertz electromagnetic wave generators/detectors and electromagnetic wave transmission paths and an integrated chip for optical interconnections that has a high speed switching feature and is adapted to use optical signals.

BRIEF DESCRIPTION OF THE DRAWINGS

FIGS. 5A and 5B are schematic illustrations of an embodiment of integrated module according to the invention and prepared in Example 3, showing the structure of the device;

DETAILED DESCRIPTION OF THE PREFERRED EMBODIMENTS

Now, the present invention will be described in greater detail by referring to the accompanying drawings that illustrate preferred embodiments of photoconductive element according to the invention and adapted to generate and detect a tera-hertz wave, although the present invention is by no means limited thereto. The applications and the properties of the generated electromagnetic wave are not limited those described in the following description.

EXAMPLE 1

Figure 1A:
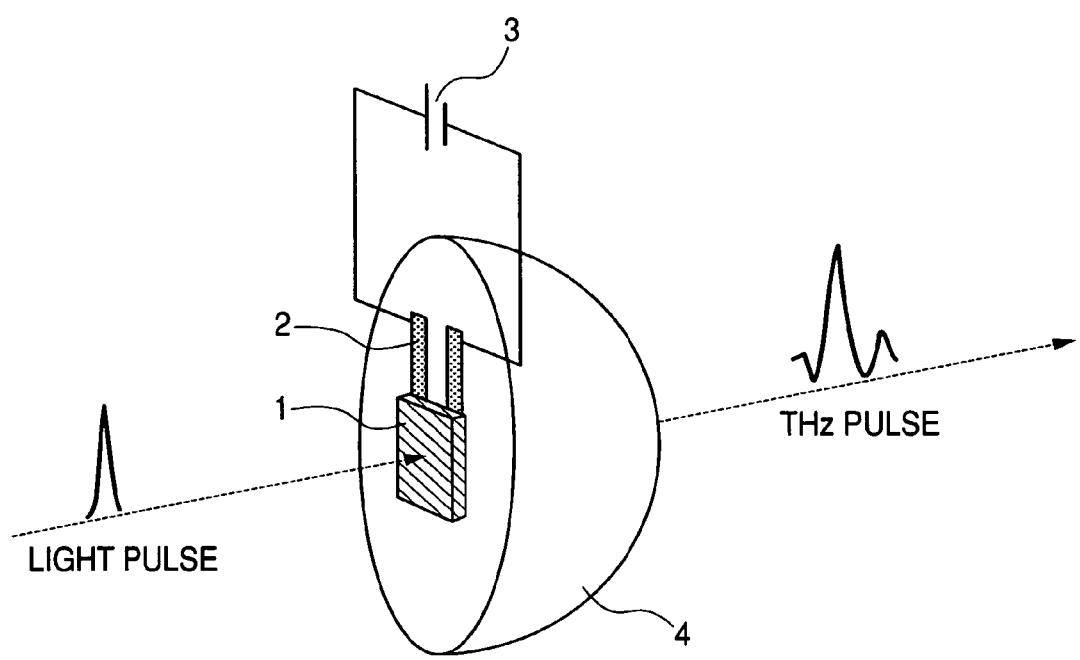
FIGS. 1A, 1B and 1C are schematic illustrations of an embodiment of integrated device according to the invention and prepared in Example 1.
Figure 1B:
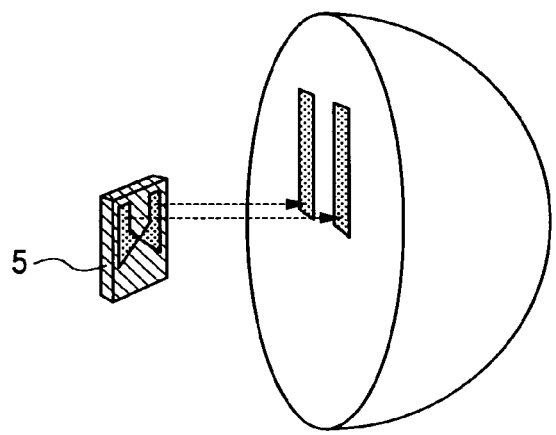

In this example, a photoconductive element is directly and integrally formed on an Si lens in order to improve the radiation efficiency from the photoconductive switch to space. FIG. 1A is a schematic perspective view of the ultimately integrally formed element. Two Ti/Au electrodes 2 are formed on the bottom surface of a semispherical lens 4 made of electrically highly resistive Si in order to supply a bias voltage. The photoconductive element 1 is integrally formed to show a configuration as illustrated in FIG. 1A where an antenna 5 is formed with a gap of 5 µm arranged to separate it into two parts on the surface of a GaAs layer grown at low temperature (LT-GaAs) as photoconductive film, as illustrated in FIG. 1B, and brought into electrode contact with bias voltage supply lines 2.

The photoconductive film shows a thickness of about 1.5 µm after removing the GaAs substrate that was used for epitaxial growth. When the photoconductive element 1 is transferred onto the Si lens, it is aligned with the Si lens in such a way that the gap of the antenna 5 lies on the center of the lens.

Now, the operation of the element will be described below. A voltage of about 10V is applied to the opposite ends of the bias voltage supply line 2 from a voltage source 3. As a laser beam is irradiated from an external femto-second laser and focused at the center of the element by means of a lens (not shown) with a pulse width of about 100 fsec, a repetition of about 80 MHz and an average power level of about 5 mW, a THz pulse can be generated with a pulse width of not greater than 1 psec as shown in FIG. 1A. The amplitude of the THz pulse is proportional to the intensity of the irradiation laser beam and the applied voltage. Therefore, it is advisable for lock-in detection to apply a sinusoidal wave signal to the voltage to be applied or modulate the power of the irradiation laser beam by means of an optical chopper.

Since the generated THz wave shows a wavelength of about 100 µm in free space and about 28 µm in GaAs, no substrate mode is practically found in the transferred GaAs film. In other words, the generated THz wave radiates totally externally. No multiple-reflection takes place because the air layer between the GaAs film and the Si lens is about 3 µm thick at most, or about 1/10 of the wavelength.

While the generation of THz wave from the photoconductive element is basically non-directional, it is possible to make the THz wave show a distribution pattern by means of the profile of the antenna. While the bowtie type antenna used in this example does not show any specific distribution pattern, it is possible to boost the propagation power of a predetermined direction by controlling the directivity of the generated THz wave by means of the Si lens. The lens can be made to show a profile other than semispherical. The aperture and the beam may be controlled by making the lens to show an aspheric profile or a super-semispherical profile.

Figure 1C:
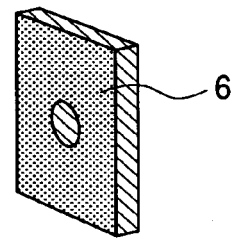

It is possible to further improve the radiation efficiency of the photoconductive element by forming an Au film 6 with a window for irradiation with a laser beam of the front surface of the photoconductive element as shown in FIG. 1C since it functions as a mirror for reflecting a THz wave. If the thickness of the Au mirror is not smaller than several µm, the mirror provides an effect of accelerating radiation of heat. Then, the photoconductive element shows improved thermal characteristics to by turn improve its radiation efficiency.

The distance by which a THz electromagnetic wave passes through the GaAs substrate is short if the THz wave is taken out by means of the above described structure. Since GaAs disperses and absorbs THz electromagnetic waves, it can deform the pulse waveform. More specifically, it can increase the pulse width, for example. Therefore, when the GaAs substrate is removed according to the invention, the generated THz electromagnetic wave passes only through the Si material that disperses THz electromagnetic waves only little so that it is possible to realize a small pulse width by means of a transmission optical system and additionally increase the intensity of the THz electromagnetic wave because the wave is absorbed only to a small extent. In an experiment, the intensity of a THz electromagnetic wave is boosted by forty times simply by removing the corresponding GaAs substrate that has a thickness of 500 µm.

Now, the process of preparing the above-described structure will be described by referring to FIGS. 2A through 2Da.

Figure 2A:
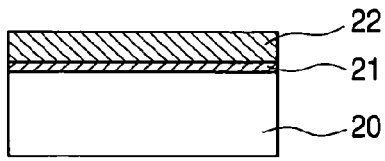
FIGS. 2A, 2B, 2Ba, 2C, 2D and 2Da are schematic illustrations of the integrated device of Example 1 in different manufacturing steps.

Referring firstly to FIG. 2A, a GaAs buffer layer (not shown), an AlAs etching stop layer 21 and a GaAs photoconductive layer 22 are made to grow on a GaAs substrate 20 typically by means of molecular beam epitaxy process. While the AlAs layer is formed by deposition at the ordinary temperature level of about 700° C., the GaAs layer is formed by deposition at a relatively low temperature level of about 250° C. to produce an LT-GaAs film. After the growth process, the work is heated in the deposition furnace at about 600° C. for the purpose of planarization of the LT-GaAs layer before it is taken out. If appropriate, the work may be annealed for another time after having been taken out from the deposition furnace.

Figure 2B:
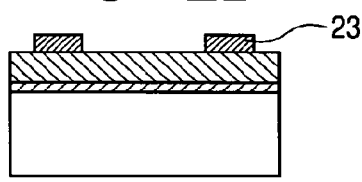
Figure 2B:
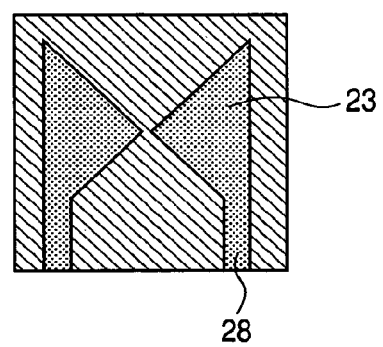

Then, referring to FIG. 2B, the work is subjected to a lift-off process, using the photoresist formed by photolithography, to form an antenna 23 of AuGeNi/Au electrodes. Ti/Au may alternatively be used to form the electrodes. While the bowties type antenna is provided with lead-out lines 28 for electrode contact, it may be replaced by a dipole type antenna provided with bias-voltage supply lines. The antenna 23 has a 5 µm wide gap at the center thereof to separate it into two parts, each of which is realized in the form of a rectangular equilateral triangle whose base side is 800 µm long and that is connected to a 50 µm wide lead-out line 28. After forming the antenna 23, it is annealed at 400° C. in order to reduce the contact resistance thereof.

Figure 2C:
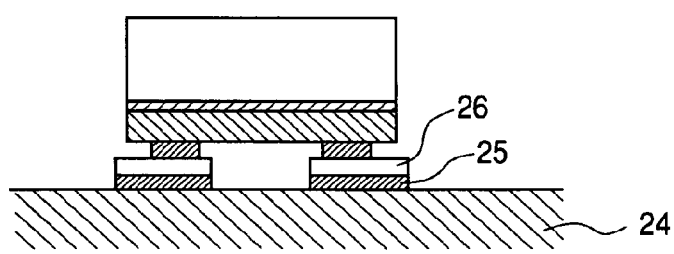

Referring to FIG. 2C, lead-out electrodes 25 (of Ti/Au) are formed on the bottom surface of the Si lens 24 and subsequently solder blocks 26 of AuSn are formed only on electrode contact portions. This structure may work well when the electric resistance of the Si is sufficiently high, although the electrodes 25 may be formed after forming an $SiO_2$ film (not shown) on the surface of the Si lens for the purpose of improving the electric insulation of the latter. The Si lens typically has a half diameter of 5 mm, although a smaller Si lens may be used for the purpose of the present invention. After cutting the GaAs wafer on which the photoconductive element is formed to a size of 1 mm square, it is bonded to the Si lens by heating it to about 300° C. under pressure, while aligning the Si lens and the photoconductive element that are held in contact with each other. A dicing saw may be used to cut the wafer. Alternatively, the substrate may be polished to a thickness of about 100 µm and cleaved to the desired size.

Figure 2D:
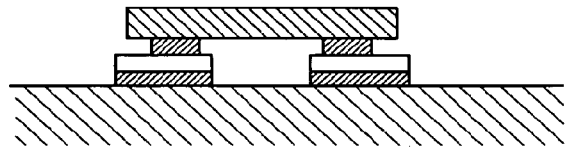
Figure 2D:
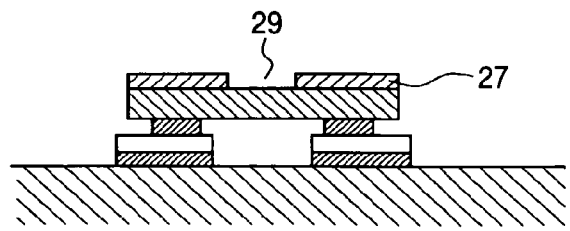

Referring to FIG. 2D, then the GaAs substrate is removed by etching. For the purpose of etching, the surrounding area is covered by resist or the like and the substrate is etched out by a mixture solution of ammonia and hydrogen peroxide. Then, the etching stops at the AlAs layer 21 so that it is possible to selectively remove the substrate. The etching rate can be controlled by controlling the temperature of the mixture solution. Then, the AlAs layer is removed by concentrated hydrochloric acid, although it may be left there without being removed.

Now, a finished film type photoconductive element is produced. However, an Au layer 27 may be formed on the surface as mirror as shown in FIG. 2Da for the purpose of effectively utilizing the THz beam of light from the side that is being irradiated with the laser beam as described above, or the side opposite to the side of the Si lens. A window 29 is formed at the center of the mirror for the irradiation of the beam.

As described above, a film type photoconductive element is directly and integrally formed on an Si lens in this example to remarkably improve the efficiency of generating a THz wave when a femto-second laser beam is irradiated.

When an electrically highly resistive Si is used as in the case of this example, Fresnel reflection is remarkable at the interface because of the high refractive index of the Si, although absorption/dispersion is slight. An organic polymer such as Teflon (registered tradename) that shows little absorption in the tera-hertz frequency range may be used instead of Si to realize a low refractive index. Then, it is possible to reduce Fresnel reflection and hence the radiation efficiency.

EXAMPLE 2

In the second example, a film type photoconductive element like the one prepared in Example 1 is bonded to a thermally highly conductive substrate in order to prevent the characteristics of the element from being degraded by elevated temperatures.

Figure 3A:
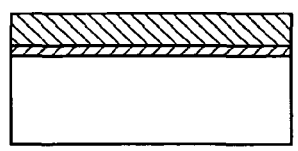
FIGS. 3A, 3B, 3C and 3D are schematic illustrations of an embodiment of integrated device according to the invention and prepared in Example 2, showing the device in different manufacturing steps.
Figure 3B:
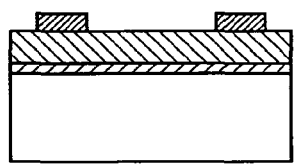
Figure 3C:
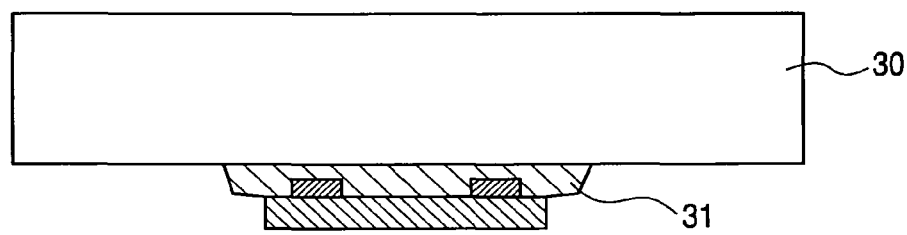
Figure 3D:
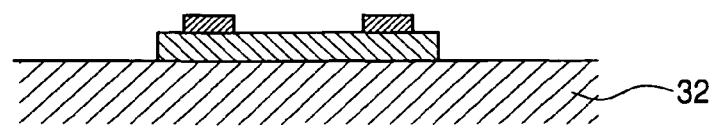

FIGS. 3A, 3B, 3C and 3D are schematic illustrations of an embodiment of integrated device according to the invention and prepared in Example 2, showing the device in different manufacturing steps. The components same as those of the embodiment of example 1 are denoted respectively by the same reference symbols and will not be described further. The process is the same as that of Example 1 down to the step of forming an antenna as shown in FIGS. 3A and 3B. Referring now to FIG. 3C, after cutting out a chip, the antenna is bonded by using a resin adhesive or the like 31 at the front surface thereof to a hold substrate 30 that is typically made of glass and then the GaAs substrate is removed by means of a technique similar to the one used in Example 1. Then, referring to FIG. 3D, the surface that appears after etching the GaAs substrate is bonded to an electrically highly resistive Si substrate 32 and subsequently the hold substrate 30 is taken out by dissolving the adhesive agent. While only van der Waals force may be used for the bonding, the work may be subjected to high temperature annealing (at a temperature higher than 500° C.) in order to raise the bonding effect after taking out the hold substrate. For the bonding, a resin adhesive or the like can be used also.

Because the element is held in contact with a substrate that shows a high thermal conductivity over the entire surface thereof, the thermal resistance of the element is reduced and the effect of the element is particularly high when the laser beam is emitted with a high output power. While the substrate may be lens-shaped as in Example 1, a high thermal conductivity substrate of MN or SiC may alternatively be used.

Figure 4A:
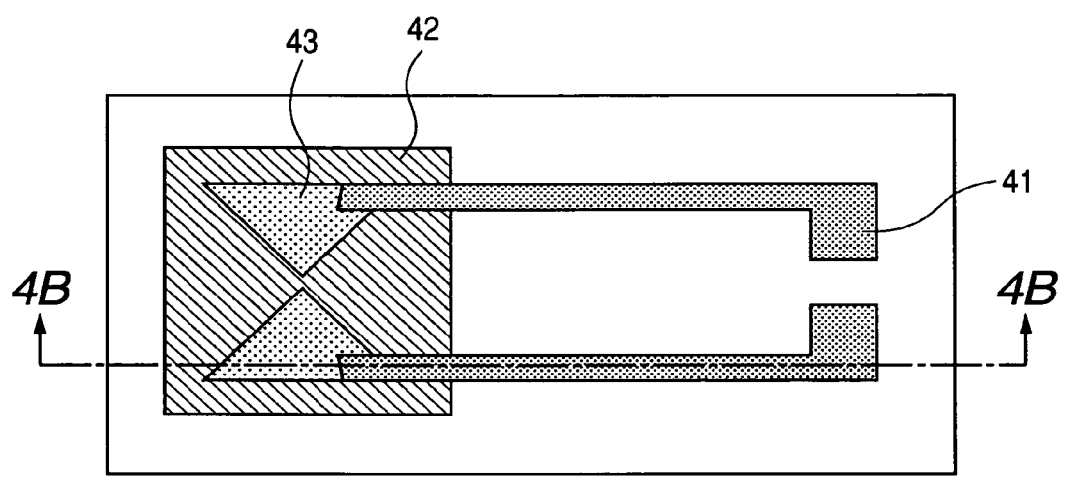
FIGS. 4A and 4B are schematic illustrations of an embodiment of integrated device according to the invention and prepared in Example 2, showing the structure of the device.
Figure 4B:
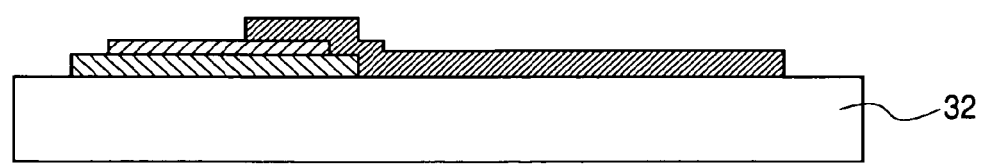

Since the antenna of the element is exposed on the surface, lead-out electrodes may be formed after forming the film-shaped photoconductive element and transferring wires 41 onto the substrate 32 as shown in FIGS. 4A and 4B if such lead-out electrodes are needed. In case the insulation is not enough to apply voltage between the electrodes, an insulation film such as $SiO_2$ film (not shown) may be formed between the wires 41 and the substrate 32. A structure similar to the above described one may also be employed when the thermal conductivity of the substrate is not very important but the influence of reflection needs to be reduced by selecting a substrate showing a low refractive index typically made of an organic polymer, onto which wires are transferred.

EXAMPLE 3

In this example, photoconductive elements according to the invention are applied to an integrated type THz wave sensing module as shown in FIGS. 5A and 5B. The configuration for the module will be described below by referring to FIG. 5A. Optical waveguides 55, 56, 62 and an optical divider/coupler 57, 58 are three-dimensionally formed in a substrate 50, which is made of a transparent polymer material such as polyimide with a modified refractive index. The work may be prepared by molding some of the components and assembling them or by using a technique of forming three-dimensional waveguides by means of a laser. Materials that can be used include quartz, glass, plastics and polymers, some of which may not be transparent. It is advisable to use a material that is practically free from loss of light at least for the waveguides. It is desirable to apply a material (not shown) that shows excellent high frequency characteristics such as polyimide or BCB to the surface where coplanar strip lines 52a, 52b are formed as high frequency lines to a thickness of not smaller than 5 µm. Additionally, it is also desirable that the substrate shows a high degree of thermal resistance when it needs to be heated after mounting the element, which will be described hereinafter.

The coplanar strip lines 52a, 52b are formed on the substrate 50 by using Ti/Au to typically show a width of 30 µm so as to be separated from each other by a gap of 200 µm. Film type photoconductive elements 51a, 51b are bonded to the lines at positions located near the opposite ends of the latter, while holding the electrodes of the elements in contact with the lines, by means of a technique same as the one described above for Example 1. The GaAs substrate of the elements has already been removed. In the case of this module, the THz wave is not taken out into space but propagated through the coplanar lines. Therefore, the electrodes of the photoconductive elements take not a role of antennas having a micro-gap but that of so many pads for contacting with the lines.

Two semiconductor lasers 53a, 53b are mounted on the rear surface side of the substrate 50. Preferably, they are surface emission type lasers that oscillate in a single mode. The oscillation wavelengths of the lasers differ from each other only slightly. Electrodes 54a through 54d are provided in order to drive the surface emission type lasers. How the laser beams emitted from the lasers are propagated will be described below by referring to FIG. 5B. The laser beam emitted from the surface emission type laser 53a is propagated through the optical waveguide 55 and irradiated onto the photoconductive element 51a. The laser beam emitted from the surface emission type laser 53b is branched into two beams by an optical divider 58 and one of the branched beams is irradiated onto the photoconductive element 51b, while the other beam is propagated through the optical waveguide 62 and mixed with the laser beam from the surface emission type laser 53a by an optical coupler 57 so as to be irradiated onto the photoconductive element 51a.

Now, the operation of the module will be described below. As a mixture of two laser beams is irradiated onto the photoconductive element 51a, it is excited at the cycle of the beat (difference cycle) component of the oscillation frequencies of the two laser beams so that, when a voltage is applied between the electrodes from the power source 59, the dipole moment is changed to generate an electromagnetic wave as a function of the beat frequency. Then, the high frequency electromagnetic wave is propagated between the coplanar lines 52a, 52b. Thus, it is possible to continuously generate a THz electromagnetic wave of a single frequency in a range between 0.1 THz and 10 THz by stabilizing the frequencies of the laser beams of the two lasers and controlling the difference of the frequencies. The propagated THz electromagnetic wave arrives at the photoconductive element 51b. The voltage generated between the opposite ends changes according to the signal of the THz electromagnetic wave because the resistance between the electrodes is reduced when they are irradiated with the laser beam from the laser 53b. In other words, it is possible to detect the THz electromagnetic wave. Then, it is possible to observe the intensity of the THz electromagnetic wave by cutting off the DC component of the output by means of capacitor 60 and amplifying the output by means of amplifier 61.

An integrated type module as described above can be used as THz sensor. When an object is placed on or near the surface of the coplanar lines 52a, 52b, the amplitude of the detected signal is changed remarkably as a function of the difference that appears in the dielectric constant and also the difference that appears in the absorption coefficient. Therefore, it is possible to observe the response spectrum that is specific to the object by changing the beat frequency. Then, it is possible to identify the object.

Figure 6:
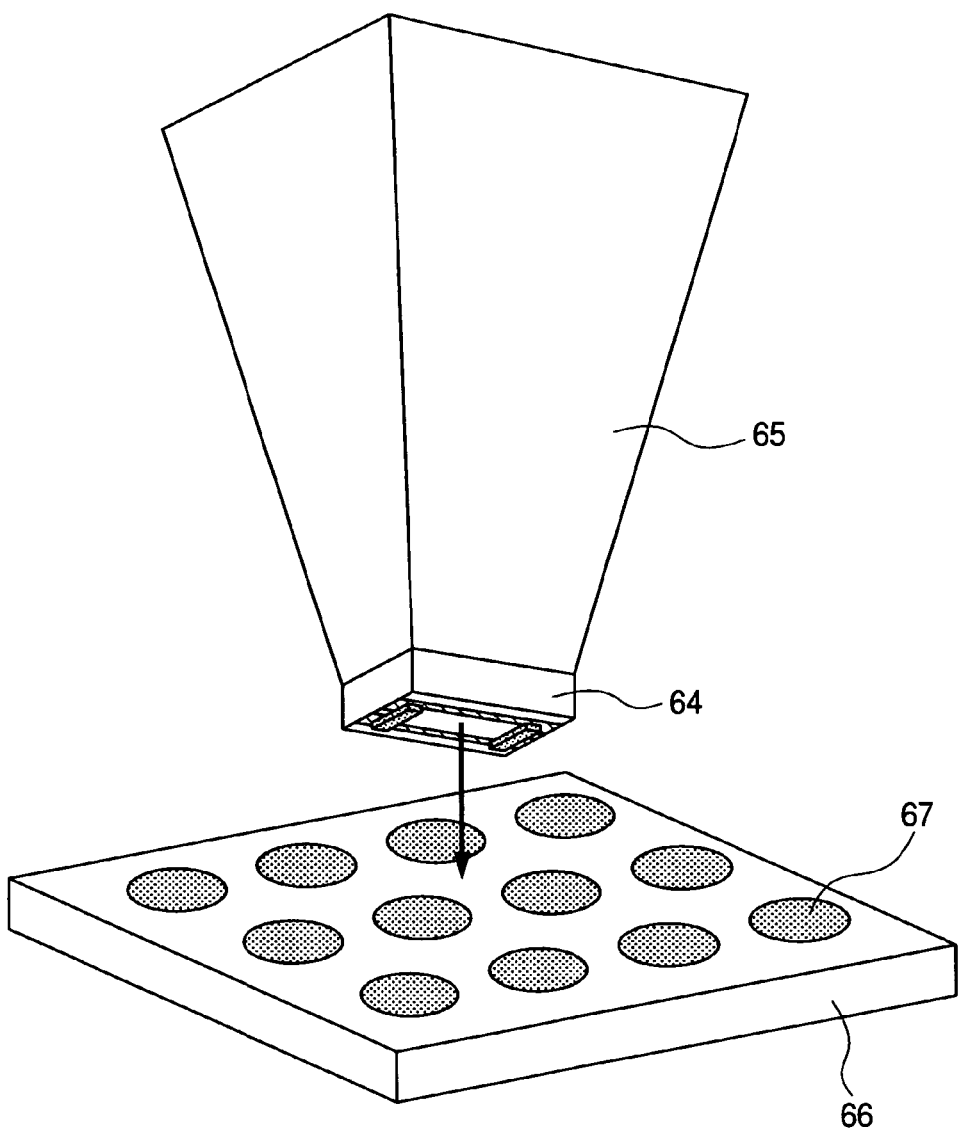
FIG. 6 is a schematic illustration of the sensing system prepared in Example 3.

FIG. 6 is a schematic illustration of the sensing system prepared by applying an integrated type module as described above. Referring to FIG. 6, 66 denotes a resin substrate or glass substrate and 67 denotes a part to which a chemical substance is applied. There are a number of such parts. As a sensor 64 prepared by integrally forming a photoconductive element according to the invention is fitted to the front end of the probe 65 and driven to scan, it is possible to examine the chemical substances that are two-dimensionally arranged in array. If the sensing system is required to operate for a DNA chip, for example, it is made to detect the part or parts that show a difference in the dielectric constant between a site where a double spiral structure is formed by hybridization and a site where such a structure is not formed. With such a technique, it is possible to identify chemical substances on a label-free basis by means of a sensing system according to the invention.

While a structure comprising integrally formed semiconductor lasers is described above, the lasers may not be formed integrally but arranged outside so as to externally irradiate the film type photoconductive elements that are produced by transfer.

EXAMPLE 4

Figure 7:
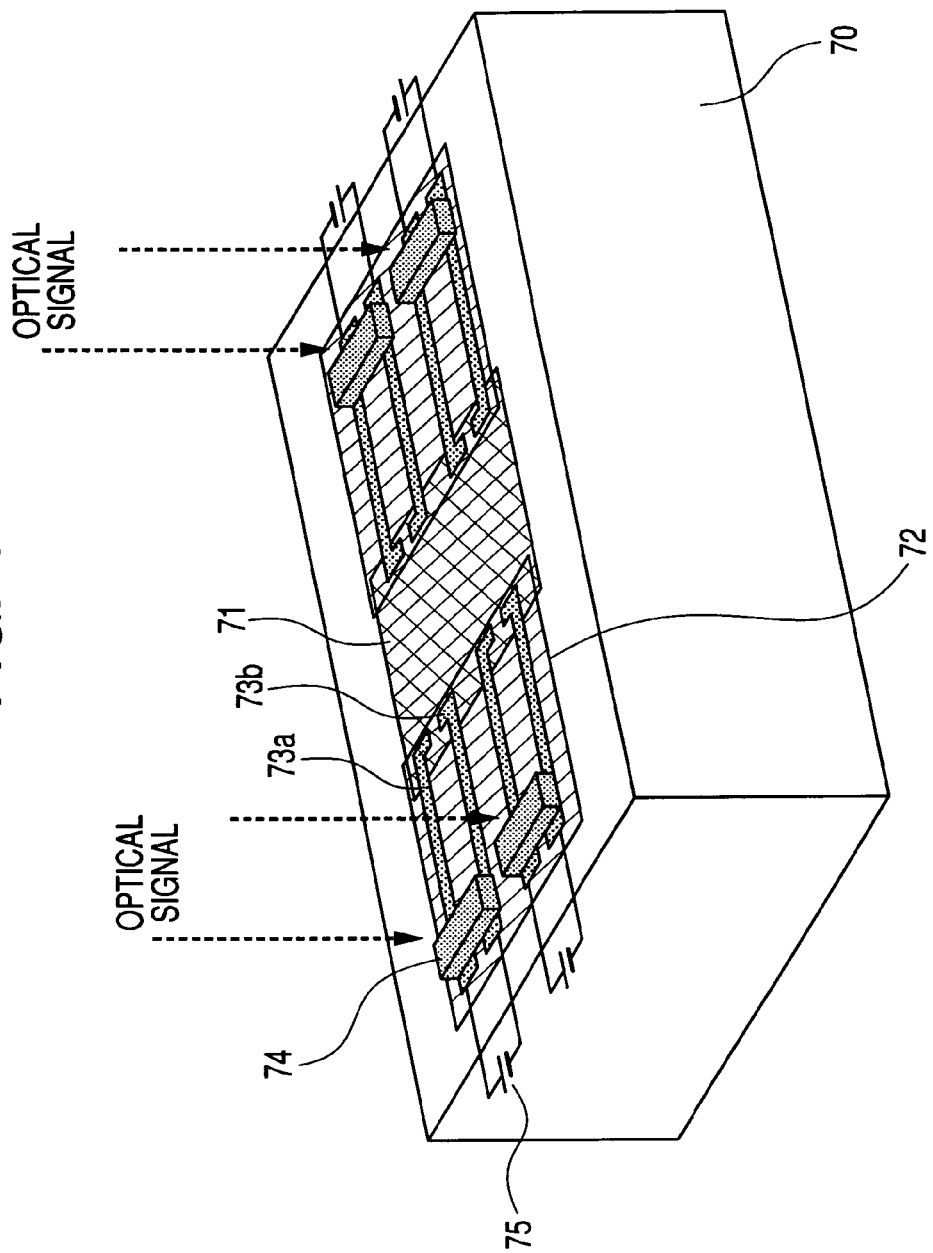
FIG. 7 is a schematic illustration of an embodiment of integrated module according to the invention and prepared in Example 4.

In this example, photoconductive elements according to the invention are applied to an optical address chip as illustrated in FIG. 7. Referring to FIG. 7, an IC is formed in region 71 on an Si substrate 70. As the photoconductive elements 74 receive an external optical signal, the signal is input to the IC and a predetermined processing operation is carried out there. In other words, a chip integrally comprises film type photoconductive elements according to the invention that operate as receiver and optically interconnect the chip with some other chip.

When the photoconductive elements 74 are not irradiated with a laser beam, each of them shows a high electric resistance so that the voltage 75 applied between lines 73a, 73b remains as the potential difference between the opposite ends of the lines. A photo-electric current flows when a laser beam is irradiated onto the photoconductive element so that the potential difference between the opposite ends of the lines comes close to nil when a resistance component (not shown) is arranged on the feeder line 73a or 73b. In short, the photoconductive element operates as a switch that responds to irradiation of a laser beam. Since the lines are connected to a specific transistor in the IC region 71, it is possible to input an optical signal to the IC and make it a high speed signal that is EMI-free and operates excellently in terms of signal integrity. In FIG. 7, 72 denotes an insulating film typically made of $SiO_2$ and adapted to reduce any leak current of the lines 73a, 73b.

The optical signal may be a signal for supplying a clock. When a device is driven to operate at high speed, it can give rise to operation errors due to disturbances of the signal applied to it if the signal is an electric signal and it is difficult to eliminate a time difference at each clock supply point because of the difficulty of wiring. However, an optical address chip does not give rise to any disturbance and the above identified problem does not arise because a clock is supplied by way of one or more than one optical waveguides that are totally different from the wiring pattern on an electric circuit substrate. While four photoconductive elements are arranged in array FIG. 7, the number of photoconductive elements that can be used for such an optical address chip is not limited.

Figure 8:
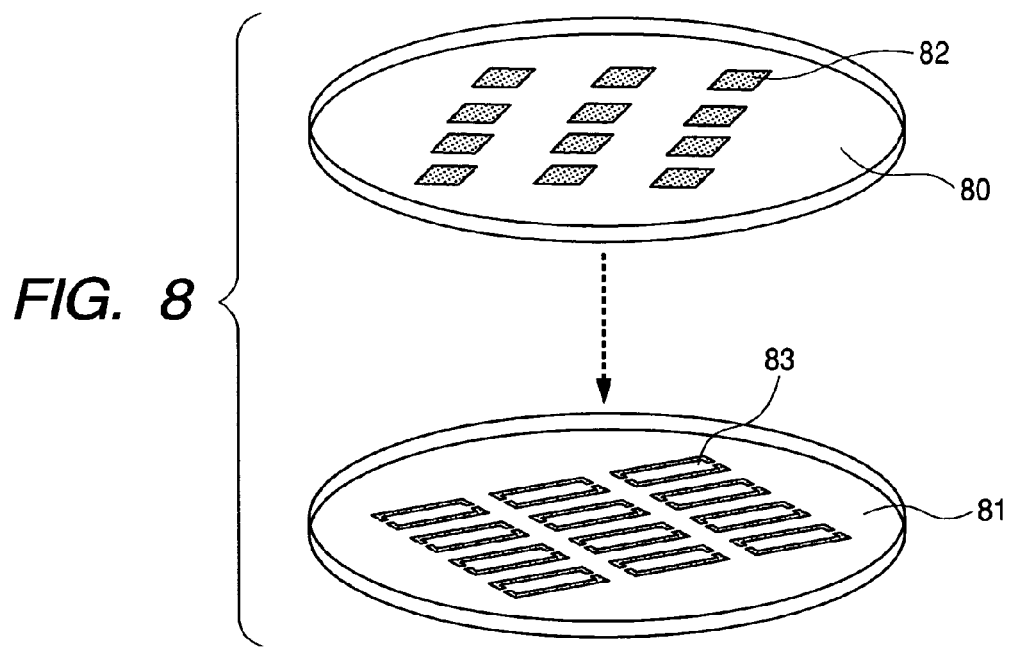
FIG. 8 is a schematic illustration of the integrated module of Example 4, showing the method of preparing the module.
Figure 9:
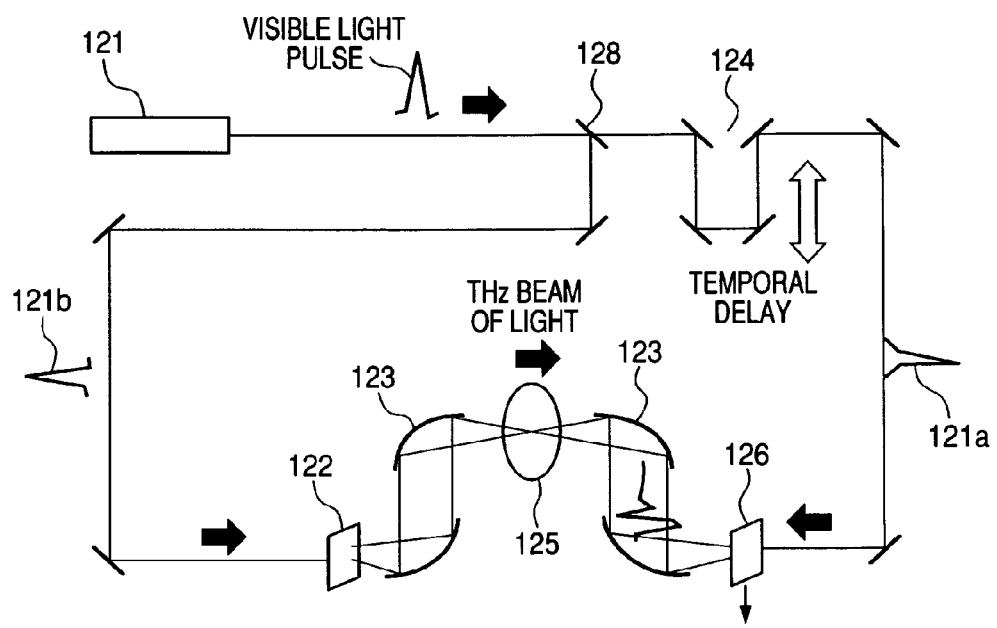
FIG. 9 is a schematic illustration of a known tera-hertz two-dimensional imaging apparatus.
Figure 10:
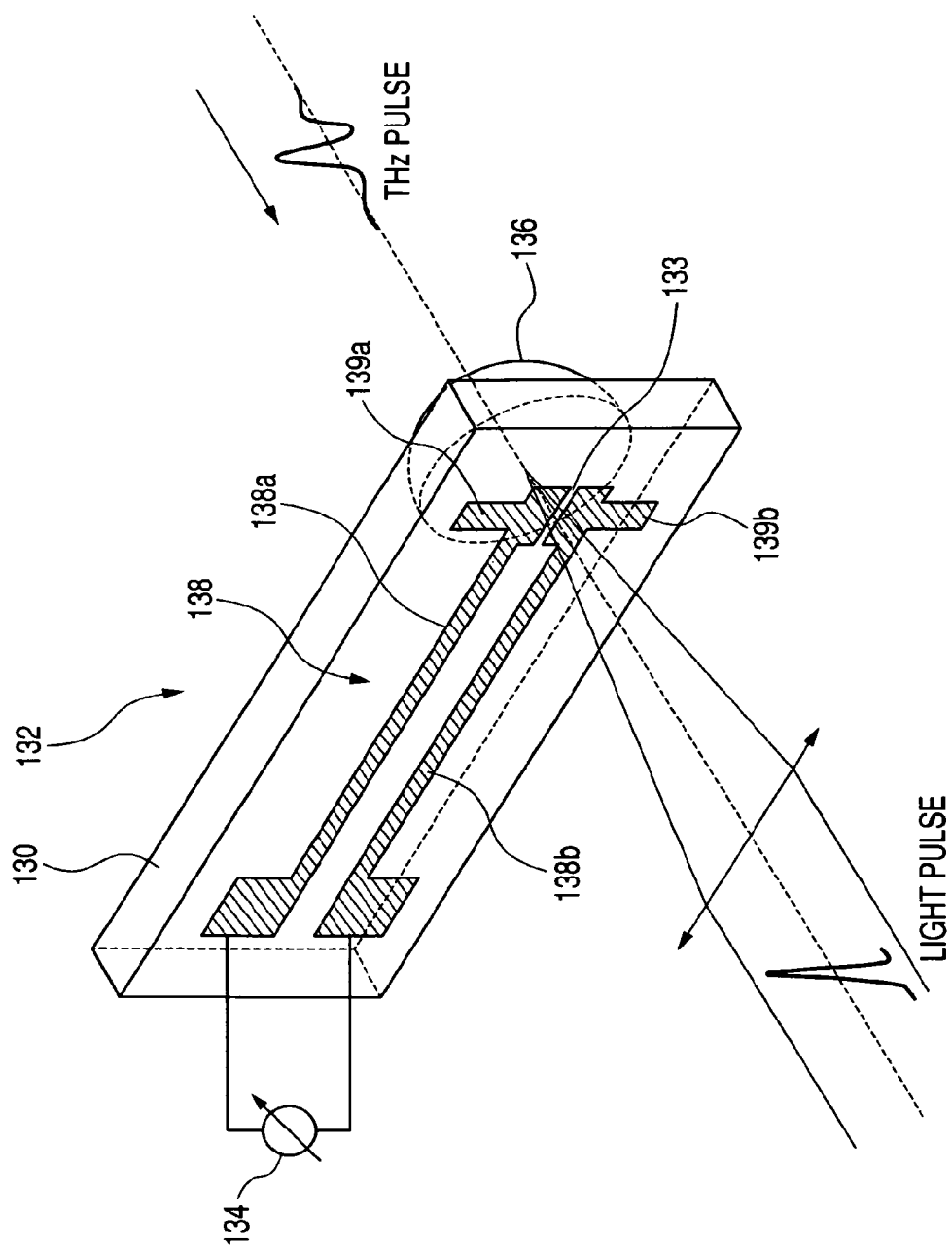
FIG. 10 is a schematic illustration of a known photoconductive element.

A method of integrally forming an array of film type photoconductive elements will be described by referring to FIG. 8. In FIG. 8, 81 denotes a substrate typically made of Si on which an IC is formed and 83 denotes a wire for transmitting an optical input signal to the IC as electric signal, while 80 denotes a hold substrate and 82 denotes a photoconductive element. The photoconductive elements 82 that are diced and integrated into a chip are arranged so as to be transferred onto the IC substrate at desired position and bonded to the hold substrate. After connecting the electrodes with AuSn arranged in between, the hold substrate is removed and the GaAs substrate is also removed by etching. The GaAs substrate may be etched to a thin film and then bonded. With the above described process it is possible to provide an integrated chip that can be optically addressed.

What is claimed is:

1. A method of manufacturing a photoconductive device comprising steps of:
   forming a photoconductive film on a first substrate;
   forming an antenna on the photoconductive film;
   forming bias voltage supply lines on a second substrate;
   arranging the first substrate having the photoconductive film and the antenna formed thereon on the second substrate having the bias voltage supply lines such that the photoconductive film, the antenna, and a portion of the bias voltage supply lines are located between the first substrate and the second substrate; and
   removing the first substrate arranged on the second substrate while leaving the photoconductive film and the antenna on the second substrate,
   wherein said antenna is brought into electrode contact with said bias voltage supply lines.

2. The method of manufacturing a photoconductive device according to claim 1, wherein the method further comprises subsequent steps of:
   arranging the second substrate having the photoconductive film and the antenna left thereon on a third substrate such that the photoconductive film and the antenna is located between the second substrate and the third substrate; and
   removing the second substrate arranged on the third substrate while leaving the photoconductive film and the antenna on the third substrate.

3. The method of manufacturing a photoconductive device according to claim 1, wherein the photoconductive film is formed on an etching stop layer formed on the first substrate, and the first substrate is subsequently removed by etching.

4. The method of manufacturing a photoconductive device according to claim 1, further comprising a step of forming an electrode on the second substrate and arranging the first substrate having the photoconductive film and the antenna formed thereon on the second substrate having the electrode formed thereon such that the antenna is brought into electrical contact with the electrode.

5. The method of manufacturing a photoconductive device according to claim 1, wherein the antenna has a gap, and the second substrate has a lens that has a center, and wherein said arranging step is conducted such that the gap of the antenna is aligned with the center of the lens.

* * * * *